United States Patent [19]

Weber et al.

[11] Patent Number: 5,481,044
[45] Date of Patent: Jan. 2, 1996

[54] PROCESS FOR THE PREPARATION OF α-ALKYL SUBSTITUTED ALDEHYDES

[75] Inventors: Jürgen Weber; Helmut Springer, both of Oberhausen, Germany

[73] Assignee: Hoechst Aktiengesellschaft, Germany

[21] Appl. No.: 356,909

[22] Filed: Dec. 15, 1994

[30] Foreign Application Priority Data

Dec. 23, 1993 [DE] Germany ............................ 43 44 064.9

[51] Int. Cl.$^6$ ........................................... C07C 45/50
[52] U.S. Cl. ................... 568/451; 568/427; 568/429; 568/450; 568/453; 585/734
[58] Field of Search .................. 568/427, 450, 568/451, 429, 453, 426; 585/671, 734

[56] References Cited

U.S. PATENT DOCUMENTS

| 4,388,476 | 6/1983 | Cooper | 568/451 |
| 4,599,458 | 7/1986 | Fischer et al. | 568/450 |
| 4,782,188 | 11/1988 | Butts | 568/444 |
| 5,082,977 | 1/1992 | Chaung | 568/454 |
| 5,387,719 | 2/1995 | Kneuper et al. | 568/455 |

Primary Examiner—Werren B. Lone
Attorney, Agent, or Firm—Jordan B. Bierman; Bierman and Muserlian

[57] ABSTRACT

α-alkyl aldehydes having 8 to 17 carbon atoms are obtained from terminal olefins containing one less carbon atom. The olefins are first isomerized in the presence of iron carbonyl and then, without separating out the iron compound, hydroformylated in the presence of rhodium as catalyst.

17 Claims, No Drawings

PROCESS FOR THE PREPARATION OF α-ALKYL SUBSTITUTED ALDEHYDES

This Application claims the benefit of the priority of German Application P 43 44 064.9, filed Dec. 23, 1993.

The Invention relates to a process for preparing α-alkyl aldehydes having from 8 to 17 carbon atoms by hydroformylation corresponding olefins containing one less carbon atom.

BACKGROUND OF THE INVENTION

Aldehydes described above are industrially important as intermediates. For example, they can be used to prepare the corresponding alcohols by hydrogenation, carboxylic acids by oxidation, and amines by aminating hydrogenation. The specified classes of compounds are used as raw materials, inter alia, for the preparation of additives for lubricants or plastics.

The preparation of aldehydes by hydroformylation of olefinically unsaturated compounds is a known reaction which is carried out industrially on a large scale in various ways. The starting materials are customarily terminal olefins which are available in large amounts as refinery products and which are predominantly converted into terminal aldehydes. However, specific applications require aldehydes branched in the α position to the carbonyl group; such aldehydes can be obtained by hydroformylation of olefins having an internal double bond.

In the processing of crude oils, olefins having an internal double bond are obtained only in limited amounts. However, they can be prepared by isomerization of olefins containing a double bond at the end of the carbon chain. This reaction is influenced by various catalysts. A known example is the isomerizing action of carbonyls of iron, cobalt, and/or nickel, which is reported by Asinger and Berg in Chem. Ber. 88,445 (1955). Manuel in JOC. 27,3941 (1962) reports similar results using iron carbonyls as catalysts. Finally, Asinger, Fell, and Collin in Chem. Ber. 96,716 (1963) describe double bond isomerization under the action of acid, basic, and neutral compounds.

Modern hydroformylation processes use as catalysts rhodium or rhodium compounds which are present in very low concentrations; i.e. in an amount of about 1 to about 20 ppm by weight, based on the olefin in the reaction mixture. To counter poisoning of the catalyst, use is made of very pure starting materials, i.e. synthesis gas and olefin. Under these circumstances, the purification of the reactants is a cost-determining factor in modern oxosynthesis. Therefore, efforts are made, by means of technical process measures or adaptation of the course of the reaction, to avoid complex purification steps without reducing the yield or the quality of the reaction product. In terms of the preparation of aldehydes branched in the α position, this requirement means that internal olefins obtained by isomerization should be able to be used in the oxosynthesis without complicated additional measures.

SUMMARY OF THE INVENTION

It is therefore an object of the Invention to combine the isomerization of terminal olefins to internal olefins and their hydroformylation to α-alkyl-branched aldehydes, in a total process which is technically simple to carry out, operates selectively, and gives the desired products in high yield.

The Invention comprises a process for preparing α-alkyl aldehydes having 8 to 17 carbon atoms by hydroformylation of olefins having from 7 to 16 carbon atoms and an internal double bond. It includes isomerizing olefins having predominantly terminal double bonds at 160° C. to 210° C. in the liquid phase in the presence of iron carbonyl and, without separating out the isomerization catalyst, hydroformylating the isomerization mixture at 80° C. to 200° C. under a pressure of 5 to 50 MPa in the presence of rhodium as catalyst.

The particular advantage of the process of the Invention lies in the direct hydroformylation of the isomerization mixture, without the necessity of prior purification of the crude product and without having to separate the isomerization catalyst. This reaction procedure is surprising in a number of respects. Thus, iron carbonyls are known as very active aldolization catalysts; hence, efforts are made to avoid contamination of the hydroformylation product with these iron compounds so as not to impair the aldehyde yield by formation of aldols. Furthermore, iron carbonyls are hydroformylation catalysts which promote the formation of straight-chain aldehydes in a manner similar to cobalt, i.e. under hydroformylation conditions, they are known to act against the isomerization of terminal olefins to internal olefins. This tendency should be reinforced by the use of rhodium as hydroformylation catalyst because, even under the action of this metal, terminal double bonds are hydroformylated more quickly than internal ones. It is therefore to be expected that the equilibrium between terminal and internal olefins will be continually shifted in favor of terminal olefins and that straight-chain aldehydes will dominate in the final product. In actual fact however, the novel process gives primarily branched aldehydes.

DETAILED DESCRIPTION OF THE INVENTION

In the first process step, α-olefin having from 7 to 16 carbon atoms in the molecule or mixtures containing such olefins are isomerized. The starting material used is the unsaturated hydrocarbon obtained, for example, by cracking of wax or by ethylene oligomerization in commercial form. Prior purification is not necessary. Depending on the desired product, olefins of uniform molecular size or olefin mixtures are used.

The isomerization is carried out in the liquid phase in the presence of iron carbonyl which is present in a concentration of 50 to 1000 ppm by weight, preferably 200 to 500 ppm by weight, based on the olefin. For the purposes of the present Invention, iron carbonyl means those carbonyl compounds which are stable under the reaction conditions, such as iron pentacarbonyl or triiron dodecacarbonyl. The reaction proceeds at temperatures of 160° C. to 210° C., preferable 170° C. to 190° C., in the liquid phase. Depending on the temperature employed and the olefin used, it is carried out at atmospheric or elevated pressure. The isomerization usually requires a reaction time of 10 to 180, in particular 30 to 60, minutes. The olefin can be dissolved in an inert solvent, e.g. in an aliphatic hydrocarbon such as cyclohexane or an aromatic hydrocarbon such as toluene, although the presence of a solvent is generally not necessary.

According to the Invention, the isomerization mixture is directly hydroformylated. The reaction of the unsaturated hydrocarbon with hydrogen and carbon monoxide is carried out at temperatures of 80° C. to 200° C. and pressures of 5 to 50 MPa in the presence of 1 to 20 ppm by weight of rhodium, based on the olefin. Particularly favorable results are obtained at reaction temperatures of 120° C. to 150° C. and pressures of 20 to 30 MPa and rhodium concentrations of 2 to 5 ppm by weight, based on the olefin.

The rhodium used as catalyst is added to the reaction mixture as metal or in the form of inorganic or organic compounds, e.g. as the oxide, trichloride, nitrate, sulfate, or ethylhexanoate. Under the reaction conditions, soluble, catalytically active rhodium carbonyl compounds are formed which can be prepared prior to the hydroformylation and added to the reaction mixture in this form. Carbon monoxide and hydrogen are used in the ratios customary in hydroformylation.

The hydroformylation of the olefins can be carried out in the presence of an inert solvent, although its presence is generally not necessary. Suitable solvents are aliphatic and aromatic hydrocarbons such as benzene, toluene, cyclohexane, and cyclic ethers such as tetrahydrofuran. It is advantageous to use the same solvent for isomerization and hydroformylation, if a solvent is used in both reaction stages.

The rhodium and the iron catalyst are separated from the aldehyde reaction product by known methods. Thus, the mere depressurization of the pressure reactor results in the catalyst being at least partially decomposed so that it can be easily filtered out. Another method of removal comprises treatment of the hydroformylation product with water or steam at elevated temperatures. It is advantageous to use 5% to 50% by volume of water, or the corresponding amount of steam, based on the reaction mixture used, and to select temperatures between 80° C. to 200° C. This causes precipitation of the metals, usually mixed with their oxides, in the aqueous phase; thus permitting them to be filtered off.

The rhodium and rhodium compounds can be separated from the iron and iron compounds, for example, by treatment of the filtration residue with a mineral acid. The rhodium-containing residue can be used again in the hydroformylation stage without special purification measures. After separating the hydroformylation product from the reaction mixture by distillation, e.g. by flash evaporation, residues of the rhodium-containing material can be recovered from the distillation residue.

The aldehydes obtained according to the Invention can be used as such or, for example, be hydrogenated to alcohols, oxidized to carboxylic acids or, by aminating hydrogenation converted to amines.

The following examples are intended to illustrate the process of the Invention, but do not limit it. All percentages and parts, unless otherwise stated, are by weight.

EXAMPLE 1

Preparation of isomeric tridecanals from 1-dodecene 2,800 g of a dodecene mixture containing 96.75% of 1-dodecene is heated to 170° C. in the presence of 1.4 g (500 ppm) of iron pentacarbonyl. The reaction is stopped after 60 minutes. This gives an isomerization mixture of isomeric dodecenes of the composition (in %):

| 1-Dodecene | 2.1 |
| --- | --- |
| 2-Dodecene | 28.8 |
| 3-Dodecene | 20.0 |
| 4-, 5-, 6-Dodecenes | 46.5 |
| Others | 2.6 |

700 g of the isomerization mixture, without separating out the isomerization catalyst and after the addition of 3.5 mg (5 ppm) of rhodium 2-ethylhexanoate, is heated to 130° C. in an autoclave in the presence of an equimolar carbon monoxide/hydrogen mixture under a pressure of 26 to 27 MPa. After gas absorption is complete (i.e. after about 1.5 hours), the reaction is stopped. The reaction product is cooled down, depressurized, distilled, after separating off the isomerization catalyst and the hydroformylation catalyst, and subsequently analyzed.

This yields, at a conversion of 99.9%, a mixture of isomeric tridecanals having the following composition (in %):

| 2-Pentyloctanal | 34.9 |
| --- | --- |
| 2-Butylnonanal | |
| 2-Propyldecanal | 15.3 |
| 2-Ethylundecanal | 16.4 |
| 2-Methyldodecanal | 23.3 |
| n-Tridecanal | 7.8 |
| Dodecene | 0.1 |
| Others | 2.2 |

EXAMPLE 2

Preparation of isomeric heptadecanals from 1-hexadecene 2116 g of a hexadecene mixture containing 92.5% of 1-hexadecene is heated to 180° C. in the presence of 1.06 g (500 ppm) of iron pentacarbonyl. The reaction is stopped after 120 minutes. This gives an isomerization mixture of isomeric hexadecenes having the following composition (in %):

| 1-Hexadecene | 5.0 |
| --- | --- |
| 2-Hexadecene | 15.1 |
| 3-Hexadecene | 12.1 |
| 4-, 5-, 6-, 7-, 8-Hexadecenes | 60.3 |
| Others | 7.5 |

1480 g of the isomerization mixture, without separating out the isomerization catalyst, and after the addition of 7.4 mg (5 ppm) of rhodium 2-ethylhexanoate, is heated to 130° C. in an autoclave in the presence of an equimolar carbon monoxide/hydrogen mixture under a pressure of 26 to 27 MPa. After gas absorption is complete (i.e. after about 1 hour), the reaction is stopped. The reaction product is cooled down, depressurized, distilled, after separating off the isomerization catalyst and the hydroformylation catalyst, and subsequently analyzed. This gives, at a conversion of 99.5%, a mixture of isomeric heptadecanals having the following composition (in %):

| 2-Heptyldecanal ) | 39.3 |
| --- | --- |
| 2-Hexylundecanal ) | |
| 2-Pentyldodecanal ) | |
| 2-Butyltridecanal | 8.3 |
| 2-Propyltetradecanal | 9.4 |

-continued

|  |  |
|---|---|
| 2-Ethylpentadecanal | 10.5 |
| 2-Methylhexadecanal | 15.9 |
| n-Heptadecanal | 7.9 |
| Others | 8.7 |

While only a limited number of specific embodiments of the present invention have been expressly disclosed, it is, nonetheless, to be broadly construed, and not to be limited except by the character of the claims appended hereto.

What we claim is:

1. A process for the preparation of α-alkyl aldehydes having 8 to 17 carbon atoms comprising isomerizing of at least one terminally unsaturated olefin at 160° C. to 210° C. in a liquid phase in the presence of iron carbonyl as an isomerization catalyst to form an isomerization mixture, said mixture comprising internally unsaturated olefins and, without separating out said isomerization catalyst, hydroformylizing of said mixture with hydrogen and carbon monoxide at 80° C. to 200° C. under 5 to 50 MPa pressure in the presence of rhodium as a hydroformylizing catalyst.

2. The process of claim 1 wherein said isomerization catalyst is present in an isomerization amount of 50 to 1000 ppm by weight, based on said terminally unsaturated olefin.

3. The process of claim 2 wherein said isomerization amount is 200 to 500 ppm by weight, based on said terminally unsaturated olefin.

4. The process of claim 1 wherein said isomerization catalyst is selected from the group consisting of iron pentacarbonyl and triiron dodecacarbonyl.

5. The process of claim 1 wherein said terminally unsaturated olefin is isomerized at 170° C. to 190° C.

6. The process of claim 1 wherein said isomerization is carried out for a period of 10 to 180 minutes.

7. The process of claim 6 wherein said period is 30 to 60 minutes.

8. The process of claim 1 wherein said isomerization is in the presence of an inert isomerization solvent.

9. The process of claim 8 wherein said isomerization solvent is selected from the group consisting of aliphatic hydrocarbons and aromatic hydrocarbons.

10. The process of claim 9 wherein said isomerization solvent is selected from the group consisting of cyclohexane and toluene.

11. The process of claim 1 wherein said mixture is hydroformylated at 120° C. to 150° C.

12. The process of claim 1 wherein said hydroformylation is in the presence of an inert hydroformylation solvent.

13. The process of claim 12 wherein said hydroformylation solvent is selected from the group consisting of aliphatic hydrocarbons, aromatic hydrocarbons, and cyclic ethers.

14. The process of claim 13 wherein said hydroformylation solvent is selected from the group consisting of benzene, toluene, cyclohexane, and tetrahydrofuran.

15. The process of claim 1 wherein said hydroformylation is carried out under 20 to 30 MPa pressure.

16. The process of claim 1 wherein said hydroformylation catalyst is present in a hydroformylation catalyst amount of 1 to 20 ppm by weight, based on said internally unsaturated olefin.

17. The process of claim 16 wherein said hydroformylation catalyst amount is 2 to 5 ppm, based on said internally unsaturated olefin.

* * * * *